United States Patent
Reese (10) Patent No.: US 11,229,581 B2
(45) Date of Patent: Jan. 25, 2022

(54) BLEEDING CONTROL DEVICE AND METHOD OF MANUFACTURE AND USE

(71) Applicant: Ryan L. Reese, Wilsonville, OR (US)

(72) Inventor: Ryan L. Reese, Wilsonville, OR (US)

(*) Notice: Subject to any disclaimer, the term of this patent is extended or adjusted under 35 U.S.C. 154(b) by 0 days.

(21) Appl. No.: 17/172,510

(22) Filed: Feb. 10, 2021

(65) Prior Publication Data

US 2021/0244625 A1    Aug. 12, 2021

Related U.S. Application Data

(60) Provisional application No. 62/972,264, filed on Feb. 10, 2020.

(51) Int. Cl.
| | |
|---|---|
| *A61K 6/50* | (2020.01) |
| *A61C 5/40* | (2017.01) |
| *A61K 47/38* | (2006.01) |
| *A61K 31/137* | (2006.01) |

(52) U.S. Cl.
CPC ............ *A61K 6/50* (2020.01); *A61C 5/40* (2017.02); *A61K 31/137* (2013.01); *A61K 47/38* (2013.01)

(58) Field of Classification Search
CPC ........................................................ A61K 6/50
See application file for complete search history.

(56) References Cited

U.S. PATENT DOCUMENTS

| | | | |
|---|---|---|---|
| 2006/0047190 A1* | 3/2006 | Jenkins | A61B 5/682 600/340 |
| 2008/0003538 A1 | 1/2008 | Wittrock | |
| 2008/0233535 A1 | 9/2008 | Lee | |
| 2019/0201164 A1 | 7/2019 | Li | |

OTHER PUBLICATIONS

Jang et al. (Restor Dent Endod. Nov. 2013; 38(4): 187-193). (Year: 2013).*
Canalda-Sahli et al (Efficacy of the glass bead sterilizer on endodontic instruments,Rev Fr Endod, Dec. 1989;8(4):29-34. English abstract from PubMed.gov). (Year: 1989).*

* cited by examiner

*Primary Examiner* — Benjamin J Packard
(74) *Attorney, Agent, or Firm* — Houda El-Jarrah; Bold Patents, PLLC (57) ABSTRACT

A bleeding control device is provided. The device includes an elongate member with a holding portion and an application portion. A known amount of hemostatic solute within a solution is administered to the application portion and allowed to dry. The elongate member is then sterilized. The resulting bleeding control device may be used during medical procedures such as root canal procedures and others.

11 Claims, 6 Drawing Sheets

BLEEDING CONTROL DEVICE AND METHOD OF MANUFACTURE AND USE

CROSS REFERENCE TO RELATED APPLICATIONS

This U.S. Non-Provisional Patent Application claims priority to U.S. Provisional Patent Application No. 62/972,264, filed Feb. 10, 2020, the entire contents of which are incorporated by reference herein for all purposes.

FIELD OF THE INVENTION

This invention relates to a bleeding control device, including a bleeding control device used for root canal procedures.

BACKGROUND

During a dental root canal procedure, it is not uncommon for the pulp within a damaged tooth to become inflamed and to bleed, filling the pulp cavity and/or the root canal with blood. When this happens, the blood may obstruct the view of the surgeon, and as such, must be removed and stopped intraoperatively. A standard methodology to control the bleeding within the canal is to wick up the blood and apply pressure to the bleeding tissue using absorbent paper points (thin cones of paper or cotton). However, this method is time consuming and generally somewhat ineffective.

With other types of dental surgeries performed outside the tooth where there is more room to work (e.g., implants, endodontic microsurgery, etc.), bleeding may be controlled and/or stopped intraoperatively by applying a solution with hemostatic properties to the bleeding tissue using cotton swabs or pellets saturated with a known concentration of the solution. However, cotton swabs and/or pellets are too large to fit within the pulp chamber and/or the root canal and are therefore inadequate for the application of such a solution during a root canal procedure.

Accordingly, there is a need for a bleeding control device that may be used intraoperatively during dental root canal procedures.

SUMMARY

According to one aspect, one or more embodiments are provided below for a bleeding control device and its method of manufacture. The method of manufacture may include providing an elongate applicator including a first end and a second end and an application portion extending from the second end to an intermediate location between the first end and the second end, forming a solution comprising a hemostatic agent solute, administering a volume of the solution to the application portion, allowing the application portion to dry, and sterilizing the bleeding control device.

In another embodiment, the method may further include providing the bleeding control device for use during a root canal procedure.

In another embodiment, the hemostatic agent includes epinephrine.

In another embodiment, the volume includes about 2.5μ-liters to 5μ-liters of solution total.

In another embodiment, the volume includes about 0.3 mg-1.5 mg of epinephrine total.

In another embodiment, the sterilizing the bleeding control device includes sterilizing the bleeding control device within an autoclave at about 250° F. for about 20 minutes.

In another embodiment, the applicator comprises cellulose and the sterilizing the bleeding control device includes sterilizing the bleeding control device within an autoclave at about 250° F. for about 20 minutes.

In another embodiment, the administering the volume of the solution to the application portion includes using a single- or multi-channel micropipette.

In another embodiment, the micropipette includes a range of about 0.5μ-liters to 10 μ-liters.

In another embodiment, the applicator includes a holder portion extending from the first end to the intermediate location and wherein the holder portion is kept free of solution.

In another embodiment, the applicator is tapered.

According to another aspect, one or more embodiments are provided below for a bleeding control device and its method of manufacture. The bleeding control device may include an elongate member including a first end and a second end and an application portion extending from the second end to an intermediate location between the first end and the second end, and a first amount of dried hemostatic agent solute configured with the application portion, and wherein the bleeding control device is sterilized.

In another embodiment, the hemostatic agent includes epinephrine.

In another embodiment, the first amount of dried hemostatic agent solute is configured with the application portion by applying a volume of solution to the application portion and allowing the volume of solution to dry.

In another embodiment, the volume of solution includes about 2.5 μ-liters to 5 μ-liters of solution total.

In another embodiment, the volume includes about 0.3 mg-1.5 mg of epinephrine total.

In another embodiment, the bleeding control device is sterilized within an autoclave at about 250° F. for about 20 minutes.

In another embodiment, the elongate member comprises cellulose and the bleeding control device is sterilized within an autoclave at about 250° F. for about 20 minutes.

In another embodiment, the elongate member includes a holder portion extending from the first end to the intermediate location and wherein the holder portion is kept free of dried hemostatic agent solute.

In another embodiment, the elongate member is tapered.

The presently disclosed bleeding control device and its method of manufacture is more fully described in the detailed description below.

BRIEF DESCRIPTION OF THE DRAWINGS

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification. None of the drawings are to scale unless specifically stated otherwise.

DETAILED DESCRIPTION OF EXEMPLARY EMBODIMENTS

In general, the device and method according to exemplary embodiments hereof includes a bleeding control device and its method of use. In some embodiments, the device may be used to reduce and/or control bleeding during endodontic surgery, endodontic microsurgery, endodontic procedures such as root canal procedures, and other types of surgeries and/or medical procedures.

For the purposes of this specification, the bleeding control device and its method of use will be described primarily in relation to its use with dental root canal procedures. However, it is understood by a person of ordinary skill in the art that the device may be used with other types of medical procedures (e.g., other types of surgeries, microsurgeries, and/or procedures) and that the scope of the device is not limited in any way by the type of procedures that it may be used with.

Figure 1:
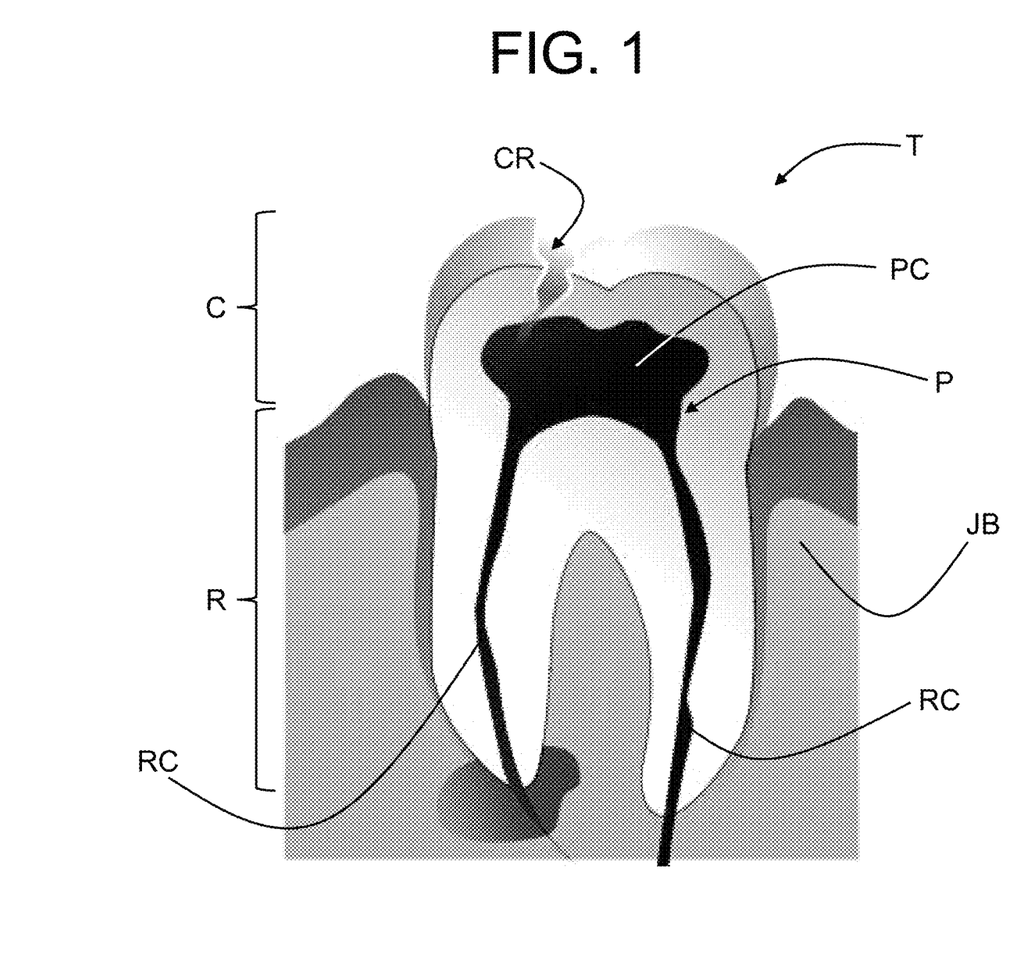
FIG. 1 shows a schematic of a human tooth in accordance with exemplary embodiments hereof.

As is known in the art, and as shown in FIG. 1, a tooth T includes a hard-upper crown C with downward extending roots R that attach the tooth T to the jawbone JB. Within the crown C is a soft-inner core known as the pulp P. The pulp P extends from pulp chamber PC beneath the upper portion of the crown C down through the root canals RC to the tip of the tooth's roots R within the jawbone JB. The pulp P includes nerve fibers, blood vessels and connective tissue.

When a tooth is cracked, has a deep cavity or sustains other types of damage as shown in FIG. 1 (indicated by the crack CR in the crown C), bacteria may enter the pulp P and will induce immediate inflammation, and left untreated, may cause an infection and/or a tooth abscess, leading to pulp death, bone loss and the potential loss of the entire tooth. One type of treatment used for this condition is a root canal procedure during which the nerve and pulp are removed, and the inside of the tooth is cleaned, reshaped, and sealed. However, during this procedure, the inflamed tooth may bleed heavily within the canal system making the procedure difficult, and as such, stopping the bleeding so that the area may be cleaned and remain free of blood is highly desirable.

Figure 2:
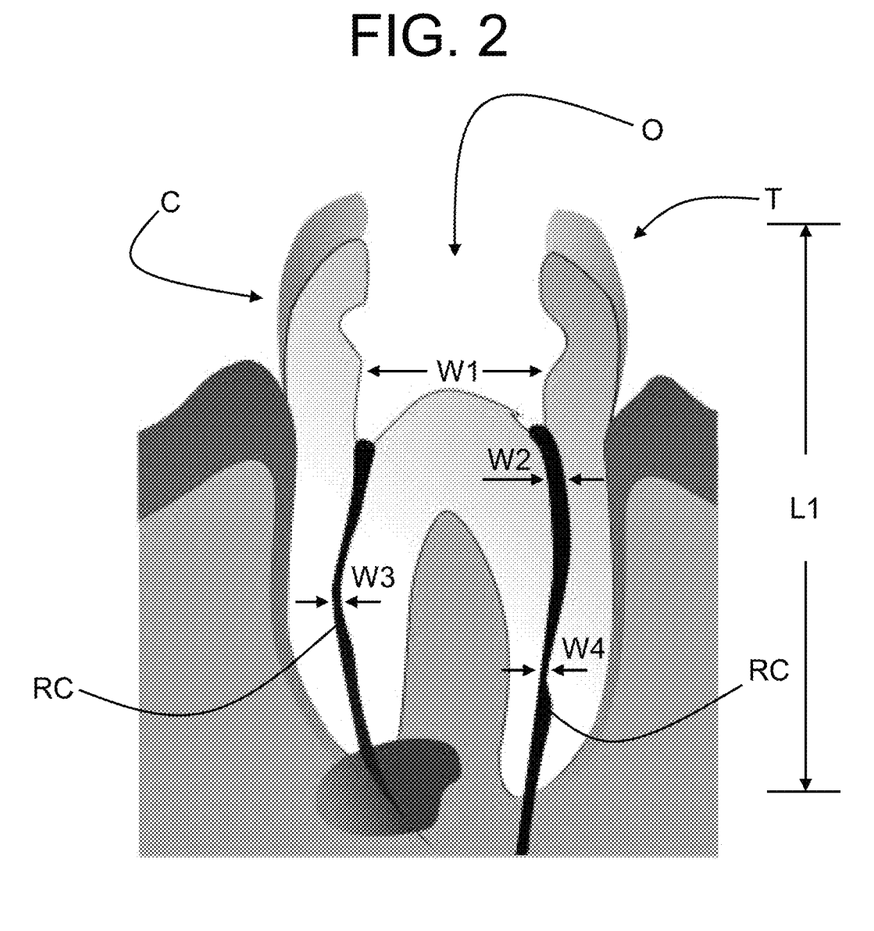
FIG. 2 shows a schematic of a human tooth prepped for root canal treatment in accordance with exemplary embodiments hereof.

As shown in FIG. 2, during the root canal procedure, an opening O is made through the crown C of the tooth T to gain access to the pulp chamber PC, and, using dental instruments, the inflamed or infected pulp P is removed from within the pulp chamber PC and root canals RC. During this process, the bleeding control device 10 described herein may be used to limit the bleeding in the area. The root canals RC are then reshaped, flushed, and cleaned, and antibacterial medicine may be applied, as necessary.

Once the root canals RC are clean, dry, and prepped, the root canal (including the pulp chamber) may be filled with dental filling (e.g., gutta percha) and sealed with a sealer paste (e.g., an epoxy-based sealer). This may prevent microleakage and recontamination by blocking the pathway of any further bacteria.

The final step of the procedure may include placing a synthetic crown (e.g., porcelain fused to metal) onto the tooth to restore the tooth's full use.

FIG. 2 depicts the combined length L1 of the tooth T and the exposed pulp chamber PC and root canals RC. FIG. 2 also shows the general width W1 of the pulp chamber PC, and several root canal widths W2, W3, and W4 that may generally represent the widths of the root canal(s) RC at various positions along the canals RC. Note that the widths of the root canal(s) RC may vary from top to bottom as demonstrated by the varying widths W2, W3, and W4 and that these widths vary from tooth to tooth and person to person.

In one exemplary embodiment hereof, the bleeding control device 10 includes an applicator 100 and a solution 200 comprising a solute 202 with hemostatic properties. The solution 200 in combination with the applicator 100 generally forms the device 10, and in use, a known concentration of the hemostatic solute 202 is provided by the tip of the applicator 100 to the desired tissue to control its bleeding. In some embodiments, the solution 200 is pre-applied to the applicator 100 during production of the device 10, while in other embodiments, the solution 200 may be applied to the applicator 100 prior to or during use by its operator. The device 10 may include other components or elements as necessary for it to fulfill its functionalities as described herein or otherwise.

Applicator 100

Figure 3:
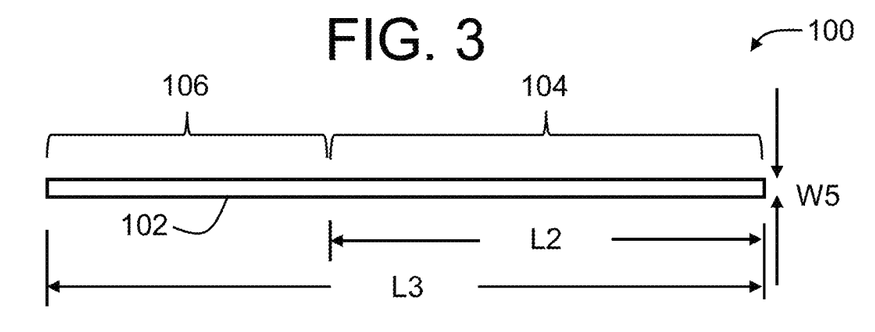
FIG. 3 shows aspects of a bleeding control device applicator in accordance with exemplary embodiments hereof.
Figure 4:
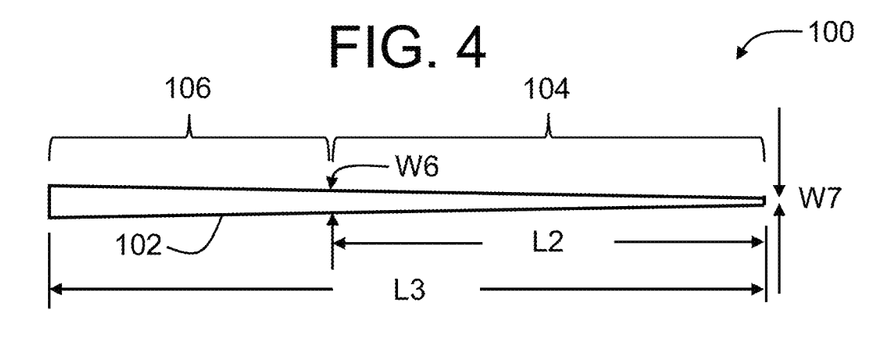
FIG. 4 shows aspects of a bleeding control device applicator in accordance with exemplary embodiments hereof.
Figure 5:
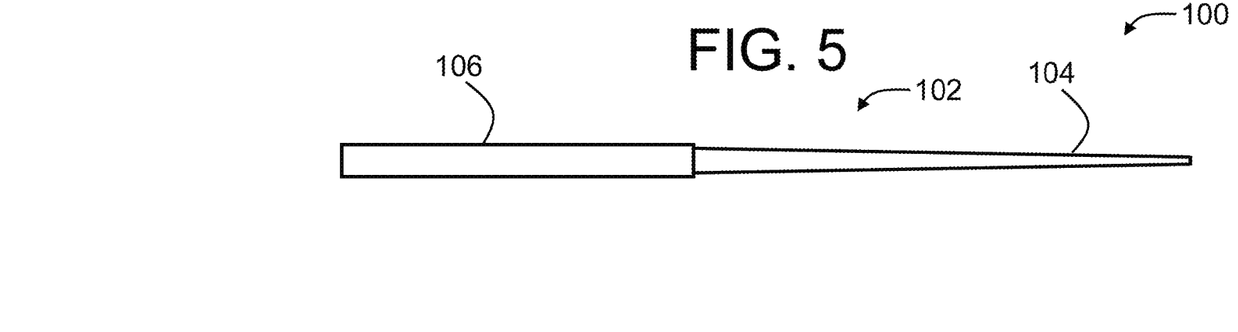
FIG. 5 shows aspects of a bleeding control device applicator in accordance with exemplary embodiments hereof.

In one exemplary embodiment hereof as shown in FIG. 3, the applicator 100 includes an elongate member such as a shaft 102 that includes an application portion 104 and a holder portion 106. In another exemplary embodiment hereof as shown in FIG. 4, the shaft 102 includes a taper from its proximal end (closest to the holder portion 106) to its distal end (closest to the application portion 104). It is understood that the shapes of the applicator 100 shown in FIGS. 3 and 4 are meant for demonstration and that the shaft 102 may include other types of shapes, forms, contours and/or tapers, and that the scope of the device 10 is not limited in any way by the shape or form of the applicator 100. For example, as shown in FIG. 5, an applicator 100 may include a straight holder portion 106 and a tapered application portion 104. In other examples, the applicator 100 may include a slightly arced application portion 104 that may facilitate the insertion of the portion 104 into a slightly arced root canal RC.

In general, the application portion 104 may be used to apply the solute 202 into the pulp chamber PC and/or root canal(s) RC, and the holder portion 106 may provide a sufficient area of the applicator 100 to be held by its operator while inserting the application portion 104 into the pulp chamber PC and/or the root canal(s) RC to apply the solute 202. As will described in other sections, the solution 200 (with the solute 202) is first applied to the applicator 100 and allowed to dry. In this way, the solute 202 may be released from the application portion 104 when wetted within the chamber PC.

Accordingly, the length L2 of the applicator's application portion 104 is preferably at least as long as the length L1 (the combined length of the pulp chamber PC and the root canal RC as shown in FIG. 2. However, it is understood that the application portion 104 may be shorter or longer than the length L1 depending on the area within the tooth to which the solute 202 is being applied.

In addition, in some embodiments, the width W5 of the FIG. 3 embodiment is preferably equal to or less than the width(s) of the root canal RC (as generally represented by widths W2, W3, and W4 in FIG. 2 so the application portion 104 may be inserted into the entirety of the root canal(s) RC without obstruction. Also, the widths W6 and W7 of the FIG. 4 embodiment are preferably equal to or less than the width(s) of the root canal RC (as generally represented by widths W2, W3 and W4 in FIG. 2 so the application portion 104 may be inserted into the entirety of the root canal(s) RC without obstruction.

In one exemplary embodiment hereof, the applicator 100 may be formed of a material suitable for insertion into the root canal(s) RC. In some embodiments, the material is compressible and may compress as it is inserted into the root canal(s) RC. Accordingly, it may be preferable that the widths W5, W6 and W7 be sized equal to, less than, or slightly larger than the width(s) of the root canal RC (e.g., widths W2, W3 and W4), and where the widths W5, W6 and W7 may be larger than the width(s) of the root canal, the applicator 100 may compress during insertion so that it may fit within the root canals RC.

In any event, it may be preferable that the application portion 104 be sized according to the same protocols as endodontic files used during the root canal procedure to ensure that the applicator 100 may properly fit within the root canals RC as required. For example, the applicator 100 may be provided in standardized sizes (as known in the art) of 08, 10, 15, 20 25, 30, 35, 40, 45, 50, 55, 60, 70, 80, 90, 100, 110, 120, 130, 140 (where the standardized sizes indicate the width of the tip of the device in one-hundredths of a millimeter), and/or with tapers of standardized ratings (as known in the art) of 02, 04 and 06 (where the standardized taper ratings indicate the increase of the width of the device traveling from the tip towards the handle in one-hundredths of a millimeter per one millimeter travel). The applicator 100 also may be provided in non-standardized sizes such as, without limitation, of Extra Course (XC), Course (C), Medium (M), Fine (F), and Extra Fine (XF), with Extra Course being the largest and Extra Fine being the smallest. The taper on non-standardized cones may be variable.

In some embodiments, the applicator 100 may comprise paper (e.g., rolled paper comprising cellulose), cotton, compressed fabric, rayon, alginate, other types of micro-fibers, plastic, other types of polymers, wood, other types of suitable materials, and any combination thereof. It is preferable that the applicator 100 may be rigid enough to be inserted into the root canals RC without kinking (even when wetted by blood or other fluids), but malleable enough to bend and conform to the shape and contour of the root canal RC as necessary during insertion. In some embodiments, the applicator 100 may comprise a core that provides rigidity to the applicator 100 and an outer layer that may hold (e.g., absorb) the solution 200 so that it may be applied during the root canal procedure as required.

Figure 6:
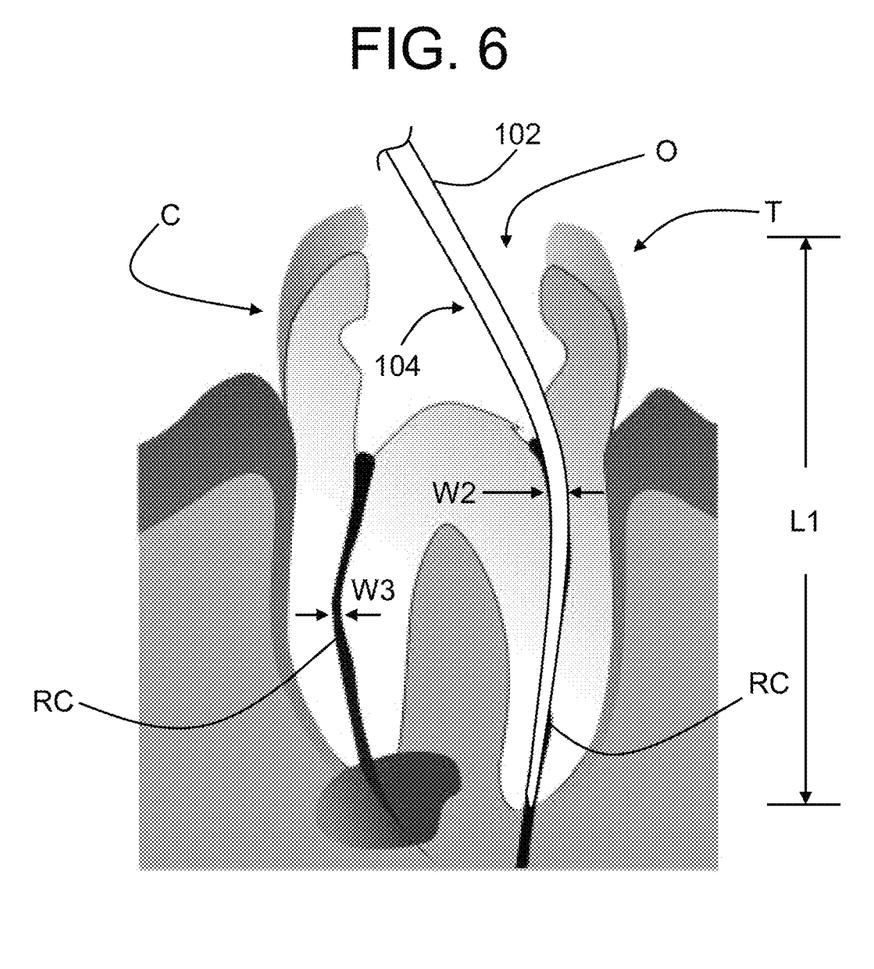
FIG. 6 shows aspects of a bleeding control device in use during a dental procedure in accordance with exemplary embodiments hereof.

FIG. 6 shows the applicator 100 inserted into the root canal RC and extending to the lower tip of the root canal RC. However, depending on the desired area of application of the solute 202, it may not be necessary for the applicator 100 to be inserted into the root canal RC to this extent. In some embodiments, the applicator 100 may include depth indicating marks that indicate the depth of the applicator 100 within the pulp chamber PC and/or the root canal(s) RC.

Solution 200

In one exemplary embodiment hereof, the hemostatic solution 200 may include a concentration of a hemostatic agent 202 (also referred to as the solute 202) that promotes hemostasis (i.e., that stops bleeding). In some embodiments the hemostatic agent 202 includes racemic epinephrine, any other agent with adequate hemostatic properties, and any combinations thereof. As is known in the art, epinephrine is known to cause minute blood vessels to constrict, thereby reducing and/or stopping the bleeding from tissues onto which it may be applied. Preservatives such as, without limitation, ascorbic acid, citric acid monohydrate, edetate disodium, and/or other preservatives also may be added to the solution 200 to prevent decomposition of the solution 200 and the solutes 202 by microbial growth, by undesirable chemical changes or by other circumstances.

Figure 7:
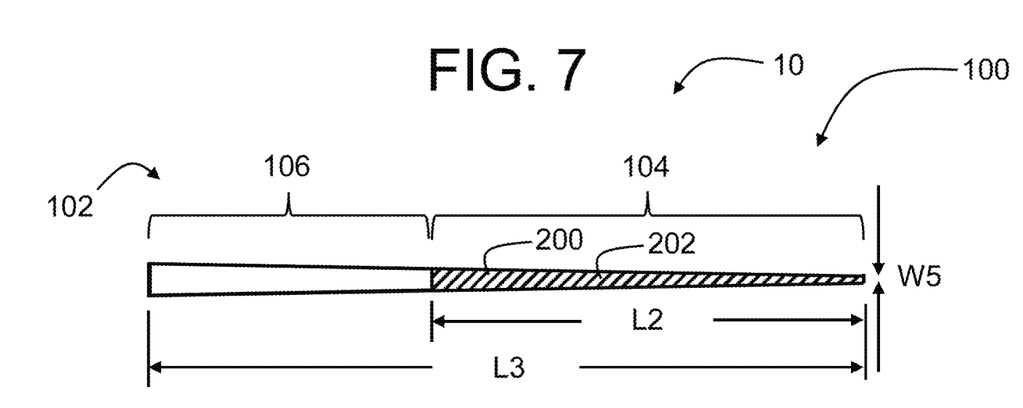
FIG. 7 shows aspects of a bleeding control device in accordance with exemplary embodiments hereof.
Figure 8:
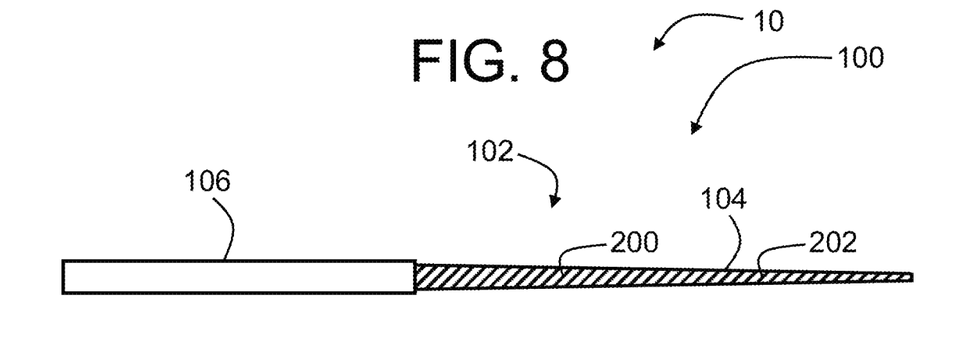
FIG. 8 shows aspects of a bleeding control device in accordance with exemplary embodiments hereof.

In some embodiments, a known amount of the solution 200 including a known concentration of the solute 202 is applied to the application portion 104 of the applicator 100 during the production of the device 10. This is represented in FIGS. 7 and 8 as the diagonal line pattern within the application portion 104 of the applicator 100.

In some embodiments, the amount of solution 200 (and therefore the amount of solute 202) that an applicator 100 may absorb will depend on the physical size and/or mass of the applicator's application portion 104. In some embodiments where the application portion 104 comprises cellulose (paper), the amount of solution 200 that the application portion 104 may absorb may depend on the volume and/or packing density of the cellulose used.

In some embodiments, a desired gram-weight of the hemostatic agent 202 is administrated to the applicator's application portion 104 via the solution 200. The desired gram-weight of the hemostatic agent 202 may depend on several factors, including, without limitation, (i) ensuring the efficacy of the treatment, and (ii) ensuring that only a safe and non-toxic level of the hemostatic agent 202 is delivered to the patient.

Dermal application of epinephrine carries a GHS Classification as a Category 2, H310, acute toxicity in accordance with 29 CFR 1920 (OSHA HCS). The Environmental Protection Agency (EPA) defines Category 2 acute toxicity as moderately toxic and moderately irritating. In larger concentrations, dermal application of epinephrine is in fact categorized by the EPA as a fatal poison.

In some embodiments, because the applicator 100 delivers the hemostatic agent 202 (epinephrine) to the patient within the tight confines of a root canal, the dose of the epinephrine must be controlled with a high level of accuracy.

First, the applicator's application portion 104 is formed to absorb a known volume $V_1$ of solution 200 without deforming or otherwise losing its physical integrity and/or the ability to perform its core functionality. Second, the solution 200 is preconcentrated to include a desired gram-weight of the hemostatic agent 202 (the dose) within that volume $V_1$. Third, the volume $V_1$ is administered to the portion 104 and the portion 104 fully absorbs the volume $V_1$. In this way, the desired gram-weight of the hemostatic agent 202 (the dose of epinephrine) is absorbed by the portion 104 and allowed to dry. Once dry, the desired gram-weight of the hemostatic agent 202 may be made available by the applicator 100 during use.

In some embodiments, a preferred volume $V_1$ is about 5µ-liters of solution 200 comprising about 1.2 mg of solute 202 (epinephrine). In other embodiments, the preferred volume $V_1$ is about 2.5µ-liters of solution 200 comprising about 0.6 mg of solute 202 (epinephrine). It is understood that other volumes $V_1$ may be used to deliver other amounts of solute 202 depending on the applicator 100 and the application of the device 10. For example, other ranges are described below.

Given the small size of the application portion 104 and the corresponding small volume of solution 200 (e.g., volume $V_1$) that the portion 104 may absorb, a micropipette may be used to accurately control of the milligrams of solution 200 being administered to an applicator's application portion 104. In some embodiments, a single- or multi-channel micropipette with a range of 0.5 µl to 10 µl may be preferable.

In some embodiments, a micropipette may be used to prepare the solution 200 at a desired preconcentration of epinephrine (or other suitable hemostatic agent), and/or to administer a preconcentrated epinephrine solution to the application portion 104 of an applicator 100. In some embodiments, a micropipette may be used to administer a preconcentrated solution 200 directly to the applicator's application portion 104. In other embodiments, the micropipette may be used to deliver a known volume of preconcentrated solution 200 to a working surface (e.g., a Teflon surface), and the application portion 104 of an applicator 10 may be drawn through the volume to absorb a known volume of solution 200. It is understood that other methods of administrating a known volume of preconcentrated solution 200 to the applicator 100 may be used, and that the scope of the device 10 is not limited in any way by the method(s) used to deliver the solution 200 to the device's applicator 100.

In some embodiments, the solution 200 comprises a volume (e.g., volume $V_1$) of preconcentrated solution 200 comprising about 0.01 mg-3.0 mg of epinephrine solute 202, and/or preferably about 0.01 mg-2.5 mg of epinephrine solute 202, and/or more preferably about 0.1 mg-2.0 mg of epinephrine solute 202, and/or more preferably about 0.1 mg-0.1.8 mg of epinephrine solute 200, and/or more preferably about 0.2 mg-1.6 mg of epinephrine solution 200, and/or more preferably about 0.3 mg-1.5 mg of epinephrine solute 202.

It is understood that application and/or measurement uncertainties may be applicable for each of the amounts and ranges described herein. For example, in some embodiments, the solution 200 may include a tolerance on the amount of solute 202 of ±0.05 mg (of epinephrine). In another example, an applicator 100 may include a tolerance on the amount of dried solute 202 of ±0.25 mg to ±0.5 mg (of epinephrine) due to propagation uncertainties within the applicator 100 during the manufacturing process. It is understood that measurement uncertainties may exist with any values described herein due to real world processes, and that the scope of the device 10 is not limited in any way by the measurement uncertainties that may be incurred.

In some embodiments, the solution 200 may be applied in liquid or gel form so that the solution 200 (and the solute 202 therein) may be absorbed by the application portion 104 and allowed to dry (and generally harden). In some embodiments, the application portion 104 is dipped into and allowed to absorb a desired volume of solution 200 (with a predetermined concentration of solute 202). In this way, the portion 104 may absorb a known amount of the solute 202. The factors that may determine the amount of solution 200 absorb include, without limitation, the applicator's material, its dimensions (e.g., width or diameter, taper), the depth to which the applicator 100 is dipped, the amount of time held within the solution 200, and other considerations, and accordingly, employing a high degree of control of these factors is preferable.

In other embodiments, a known volume of solution 200 with a known concentration of solute 202 is administrated to the applicator's application portion 104 for absorption. In this embodiment, it may be preferable that the entire volume of solution 200 be absorbed by the portion 104. In this way, a known amount of the solute 202 also may be administered and held by the application portion 104.

In some embodiments, the application portion 104 (or at least an outer portion of the application portion 104) may be saturated by a known amount and/or concentration of the solution 200 and allowed to dry. In some embodiments, the solution 200 may form a coating on the outer surface of the application portion 104 and allowed to dry.

Once dry, it is preferable that the hemostatic agent 202 remain intact on the applicator 100 until being rewetted during use (e.g., rewetted by blood or other fluids within the pulp chamber PC and/or the root canals RC). For example, it is preferable that the known amount and/or concentration of the hemostatic agent 202 on the application portion 104 generally remain on the application portion 104 during sterilization, packaging, transport to the end user, storage, etc. and until use of the device 10. In this way, the known amount and/or concentration of the hemostatic agent 202 may generally remain unchanged from the time of production of the device 10 to the time of usage of the device 10.

Once rewetted, the hemostatic agent 202 may release from the applicator 100 and be applied to tissue in contact with or within close proximity to the application portion 104.

It is understood that other techniques of applying and holding stable a known amount and/or concentration of the hemostatic agent 202 to the application portion 104 of the device 10 may be used as is known in the art, and that the scope of the device 10 is not limited in any way by the way in which the solution 200 is applied and held in place on the applicator 100.

In some embodiments, before, during and/or after production of the device 10, the amount and/or concentration of the hemostatic agent 202 within the solution 200 and/or on the application portion 104 of the device 10 may be quantified to ensure adherence to the designed dosage and/or usage levels, as well as medical industry standards and protocols for the solution 200 and the hemostatic agent 202.

In some embodiments, the amount and/or concentration of the hemostatic agent 202 within the solution 200 may be measured using an optical detection system such as a spectrophotometer, fluorometer, colorimeter, HPLC, or other type(s) of test systems. In some embodiments, the optical detection system is adapted to measure reflectance, transmittance, and/or absorbance properties of the solution 200 to determine its amount and/or concentration of solutes 202. It is understood that other types of tests and measurements may be employed to determine the amount and/or concentration of the solution 200 on the applicator 100.

Figure 9:
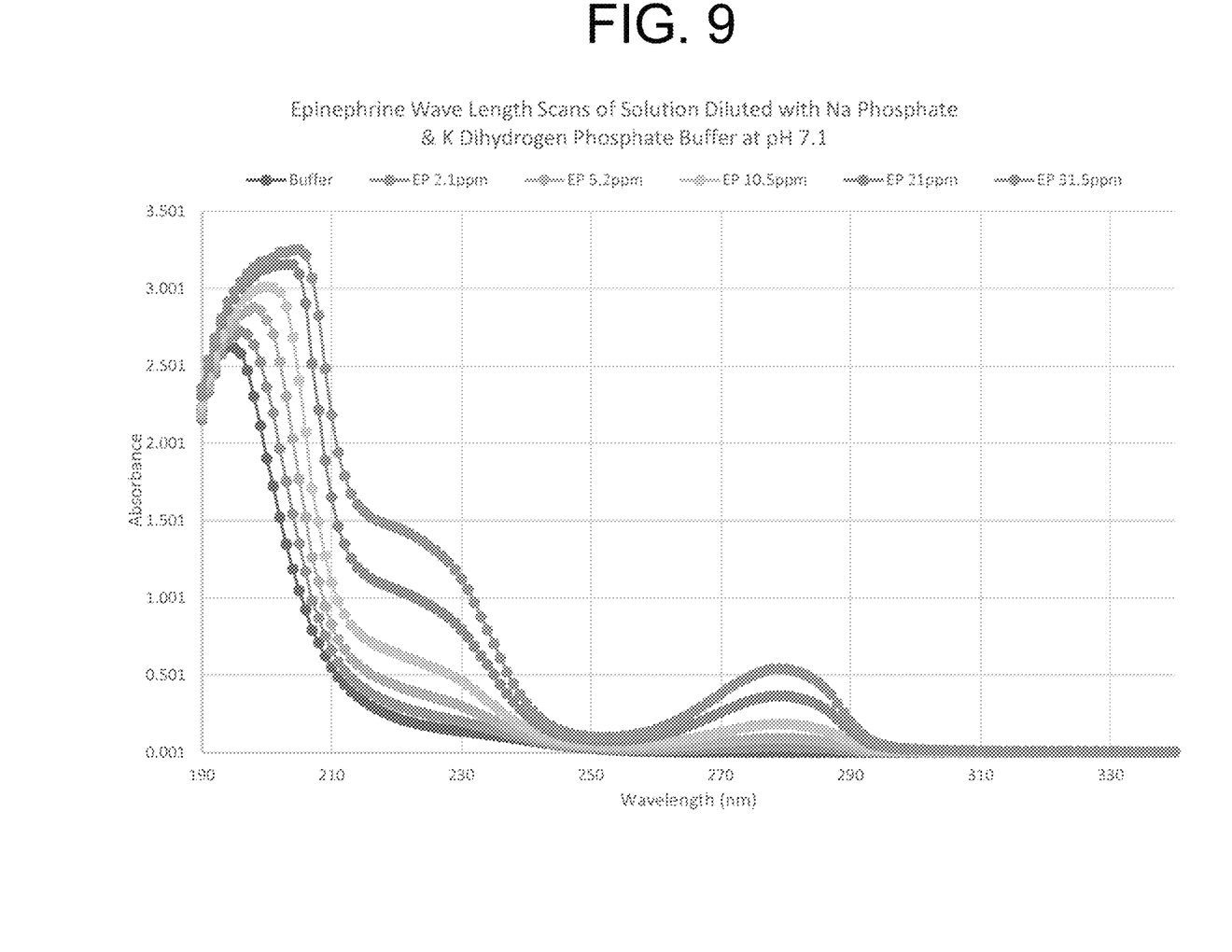
FIG. 9 shows aspects of solute concentration measurement results in accordance with exemplary embodiments hereof.

As is known in the art, a spectrophotometer measures the amount of light that may pass through a solution. Depending on the constituents of the solution, different wavelengths of light may be absorbed by the solution while other wavelengths may pass through the solution. In one example, a solution including epinephrine was tested using a spectrophotometer (e.g., a HACH 6000 UV-VIS spectrophotometer) and the results are shown in FIG. 9. As seen, epinephrine absorbs wavelengths in the 260 nm to 290 nm range with a peak at about 280 nm. In this way, the concentration levels of hemostatic agent 202 (epinephrine) within the solution 200 may be measured at any stage of production of the device 10 using this preferred method.

Sterilization

In some embodiments, the device 10 may be sterilized during or after production and packaged in sterilized packaging before being provided to the user. As is known in the art, it is preferable to only use sterilized and/or cleaned instruments while performing any type of surgical procedure on the human body. The device 10 may be sterilized using any known sterilization technique as is known in the art.

A first method used to sterilize items required in the medical industry includes using a glass bead sterilizer. A standard temperature used by a glass bead sterilizer is about 425° F. During this process, the item to be sterilized is placed within the sterilizer for about 5-10 seconds.

In a first test performed, a standard applicator 100 without epinephrine was sterilized using a glass bead sterilizer at 425° F. The sterilization was successful and the applicator 100 was undamaged.

In a second test performed, a standard applicator 100 dosed with a solution of the hemostatic solution 200 including racemic epinephrine was sterilized using a glass bead sterilizer at 425° F. for 5-10 seconds. The sterilization resulted in discoloration of the applicator 100 (the applicator 100 turned a darkened, brownish color). Additional applicators 100 dosed with the solution 200 were subsequently sterilized using the same methodology and with the same results.

The melting point of racemic epinephrine is known to be about 410° F.-415° F. and the melting point of the applicator 100 (non-dosed) is about 500° F.-518° F. Accordingly, it is believed that bringing the solution 200 and the applicator 100 to 425° F. within the glass bead sterilizer exceeded the melting point of the solute 202 within the solution 200 resulting in the discoloration of the applicator 100. In addition, preservatives within the solution 100 also may have been affected by the high temperature. Given the above, it is deemed that using a glass bead sterilizer for the sterilization of the applicator 100 and solution 200 combination is not a preferred sterilization methodology.

A second method used to sterilize items required in the medical industry includes using an autoclave sterilizer. Autoclave sterilizers utilize pressurized saturated steam (at its equilibrium point) at about 121° C. (250° F.) for about 15-20 minutes depending on the load and the contents being sterilized. As is known in the art, because autoclaves use damp heat (steam) to kill bacteria and other microorganisms, heat-labile products such as plastics may melt and paper products may be deformed or otherwise damaged during this type of sterilization process, rendering the autoclave a non-preferred sterilization process for such types of items.

In a third test performed, an applicator 100 dosed with the solution 200 was sterilized using an autoclave at about 250° F. for about 20 minutes. The expected results were that the high temperature and high pressurized steam inflicted upon the applicator 100 by the autoclave would severely compromise the physical integrity of the paper-based applicator 100. However, the test resulted in unexpected results. After the sterilization process, the solution dosed applicator 100 was allowed to dry within the sterilization pouch for several hours (e.g., for 1-2 hours), after which the applicator 100 was inspected and deemed fully functional. Accordingly, the use of an autoclave for the sterilization of the applicator 100 and solution 200 combination is unexpectedly a preferred sterilization process.

It is understood that any aspect or element of any embodiment described herein or otherwise may be combined with any other aspect or element of any other embodiment to form additional embodiments of the device 10, all of which are within the scope of the device 10.

Where a process is described herein, those of ordinary skill in the art will appreciate that the process may operate without any user intervention. In another embodiment, the process includes some human intervention (e.g., a step is performed by or with the assistance of a human).

As used in this description, the term "portion" means some or all. So, for example, "A portion of X" may include some of "X" or all of "X". In the context of a conversation, the term "portion" means some or all of the conversation.

As used herein, including in the claims, the phrase "at least some" means "one or more," and includes the case of only one. Thus, e.g., the phrase "at least some ABCs" means "one or more ABCs," and includes the case of only one ABC.

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only," the phrase "based on X" does not mean "based only on X."

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

As used herein, including in the claims, a list may include only one item, and, unless otherwise stated, a list of multiple items need not be ordered in any particular manner. A list may include duplicate items. For example, as used herein, the phrase "a list of XYZs" may include one or more "XYZs".

It should be appreciated that the words "first" and "second" in the description and claims are used to distinguish or identify, and not to show a serial or numerical limitation. Similarly, the use of letter or numerical labels (such as "(a)", "(b)", and the like) are used to help distinguish and/or identify, and not to show any serial or numerical limitation or ordering.

No ordering is implied by any of the labeled boxes in any of the flow diagrams unless specifically shown and stated. When disconnected boxes are shown in a diagram, the activities associated with those boxes may be performed in any order, including fully or partially in parallel.

While the invention has been described in connection with what is presently considered to be the most practical and preferred embodiments, it is to be understood that the The invention is not to be limited to the disclosed embodiments, but on the contrary, is intended to cover various modifications and equivalent arrangements included within the spirit and scope of the appended claims.

The invention claimed is:

1. A method of making a bleeding control device, the method comprising:
   (A) providing an elongate applicator comprising cellulose and including a first end and a second end and an application portion extending from the second end to an intermediate location between the first end and the second end;
   (B) forming a solution comprising a hemostatic agent solute including epinephrine;
   (C) administering a volume of the solution to the application portion;
   (D) allowing the application portion to dry;
   (E) sterilizing the bleeding control device using an autoclave;
   (F) allowing the sterilized bleeding control device from (E) to dry within a holder adapted to keep the bleeding control device straight.

2. The method of claim 1 further comprising:
   (G) providing the bleeding control device for use during a root canal procedure.

3. The method of claim 1 wherein the volume includes about 2.5μ-liters to 5μ-liters of solution total.

4. The method of claim 1 wherein the solution total volume includes about 0.3 mg-1.5 mg of the epinephrine total.

5. The method of claim 1 wherein the sterilizing the bleeding control device in (E) includes sterilizing the bleeding control device within the autoclave at about 250° F. for about 20 minutes.

6. The method of claim 1 wherein the administering the volume of the solution to the application portion in (C) includes using a single- or multi-channel micropipette.

7. The method of claim 6 wherein the micropipette includes a volume range of about 0.5μ-liters to 10μ-liters.

8. The method of claim 1 wherein the applicator includes a holder portion extending from the first end to the intermediate location and wherein the holder portion is kept free of solution.

9. The method of claim 1 wherein the applicator is tapered.

10. The method of claim 1 wherein the elongate applicator includes a core extending at least partially between the first end and the second end and that provides rigidity to the elongate applicator.

11. The method of claim 1 wherein the elongate applicator includes at least one depth indicating mark.

* * * * *